US006949637B2

(12) United States Patent
Lilly et al.

(10) Patent No.: US 6,949,637 B2
(45) Date of Patent: Sep. 27, 2005

(54) METHODS FOR DIAGNOSIS, PREDICTION AND TREATMENT OF ASTHMA AND OTHER INFLAMMATORY CONDITIONS BASED ON EOTAXIN CODING SEQUENCE POLYMORPHISM

(75) Inventors: Craig M. Lilly, Concord, MA (US); Andrew D. Luster, Wellesley, MA (US); Jeffrey M. Drazen, Winchester, MA (US)

(73) Assignees: Brigham and Women's Hospital, Inc., Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 10/413,255

(22) Filed: Apr. 14, 2003

(65) Prior Publication Data

US 2003/0165980 A1 Sep. 4, 2003

Related U.S. Application Data

(62) Division of application No. 09/076,259, filed on May 12, 1998, now Pat. No. 6,548,245.
(60) Provisional application No. 60/046,720, filed on May 16, 1997.

(51) Int. Cl.[7] ............................................. C12H 21/04
(52) U.S. Cl. ................. 536/24.33; 536/23.5; 536/24.1; 536/24.3
(58) Field of Search ........................... 536/23.5, 24.33, 536/24.1, 24.3

(56) References Cited

U.S. PATENT DOCUMENTS 6,403,782 B1 * 6/2002 Luster et al. .............. 536/23.5

OTHER PUBLICATIONS

Garcia–Zepeda et al. Genomic organization, complete sequence, and chromosomal location of the gene for human eotaxin (SCYA11), an eosinophil–specific CC chemokine. Genomics. May 1, 1997;41(3):471–6.*
Bartels et al. Human dermal fibroblasts express eotaxin: molecular cloning, mRNA expression, and identification of eotaxin sequence variants. Biochem Biophys Res Commun. Aug. 23, 1996;225(3):1045–51.*
Entrez Nucleotide Database Accession No. HSU46572 (published May 13, 1997).*
Entrez Nucleotide Database Accession No. AA125790 (last updated Nov. 26, 1996).*
U.S. Appl. No. 60/000,449.*

* cited by examiner

*Primary Examiner*—David Guzo
*Assistant Examiner*—Daniel M. Sullivan
(74) *Attorney, Agent, or Firm*—Wolf, Greenfield & Sacks, P.C.

(57) ABSTRACT

Methods and compositions for diagnosing and treating asthma are provided. The methods involve the discovery of a correlation between an eotaxin gene polymorphism and the ocurrence of asthma.

2 Claims, 2 Drawing Sheets

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 4119 base pairs
      (B) TYPE: nucleic acid
      (C) STRANDEDNESS: single
      (D) TOPOLOGY: linear (xi) SEQUENCE DESCRIPTION: SEQ ID NO: 1:

```
AGGTTCTACA TTAGACTAAC CCACCGGGAA TGGAGCAGGA AGAACAGGG AAGACTCCA      60

ATTTTTGGCC TCTATTTGGT AATTATAGTT AACTTTTTAG GTAATTATAG ACCAATTA     120

CTAGATGGGC ACTTAGAGAC TTTGCAGGAC AGCAAGAGCT GTCTCTAATC CTGTGCCC     180

GACAGACATC ACCAGTCAAC CACAACACAG TATTTAACTA ACGCAAGTCA ACTCCTCA     240

ATCTTTAACA TTCTTGTTTG TGCTACTGTA CCAATCAATC AATTTGATAT GAGAGTGT     300

AGGAAAAAAC AGGAAACAGG TTTGCAGTAC CTCCACACCA GTATTCAATG CTGTAATC     360

CTGCAGTGAC TCCATTAAAG ACTTTGCCTC CCTTATACCC TCTCCAACTA GGGTGCCT     420

TGTTATGAAC AAAGGGATAT GTATAGGTTC TTGTGTTGCC TCTCTCTTTG ATATTTTT     480

CCATCAGATA CCTTGTCTGC AATGTGTGCT CAGAGAGTGA GGGGGGAACT AGATGATT     540

TTTTCCAAAT GTGTTCCCTA AATGTGTTCC CTGGGGAATA AGGGCACGAG AGGCTGCC     600

TTCTATTTCA AACAAATCCC CTTCACTACA GTGTATTTGA TGAGTTGGGG TTTGTTTT     660

TTCCATTTGG AAAAGGGCTT TAGCAGCTAA GCAAATGGTT TTAAAGTGCC TCAGAAGT     720

AGATTAATAG AAACTATCCA GTTCTGATGT CCTATCATGC TAAAATTTCA GGGACTAA     780

TTCTGTGATC ATTACATTGA AACACAGCAG CAAAGCTGTG GTGTGTTGTC CTTCCTGG     840

CAGAGATGCA ACTATGTGCA GGGCTGCTGA GCTCTCTCTG CATCTGGGTG GGAGCCTA     900

GGAAGTTTTG GGGCTCCTTC CTGGTCTCCA AAATCCTCAA GACCACCATG TGAACACA     960

AATCAAGGAA GGTTCTTAGA TCGACTCATC CCCCAGGCCT TTGGTTTCCT TGCTCTT     1020

CCCAACTACA GGTGTTTCAT TTCAACTCAT CCCCTAGGGC CTTGGTTTTC TTGCTCT     1080

CCCCCACTAC AGATGTTTAA CTTCATTTCA TAACCACATA TTCCCCTCCT TTTCCAA     1140

AAGATCCAGA TGGATTAAAA AATGTACCAA GTCCCTCCTA CTAGCTTGCC TCTCTTC     1200

TCTGCTTGAC TTCCTAGGAT CTGGAATCTG GTCAGCAATC AGGAATCCCT TCATCGT     1260

CCCCGCATGG GCAAAGGCTT CCCTGGAATC TCCCACACTG TCTGCTCCCT ATAAAAG     1320
```

-continued

| | | | | | |
|---|---|---|---|---|---|
| GGCAGATGGG | CCAGAGGAGC | AGAGAGGCTG | AGACCAACCC | AGAAACCACC | ACCTCTC | 1380 |
| CCAAAGCTCA | CACCTTCAGC | CTCCAACATG | AAGGTCTCCG | CAGCACTTCT | GTGGCTG | 1440 |
| CTCATAGCAG | CTGCCTTCAG | CCCCCAGGGG | CTCGCTGGGC | CAGGTAAGCC | CCCCAAC | 1500 |
| TTACAGGAAA | GGTAAGGTAA | CCACCTCCAG | AGCTACTAGG | TCAGCAAGAA | TCTTTAC | 1560 |
| CTCACTGCAA | ATTCTCCATT | TGAAAAATAG | GGAAACAGGT | TTTGTGGGTG | GACAAGA | 1620 |
| GCCTCAACCT | CACATCCAGT | CACTGGAAGA | GCCAGAACTA | GAAAGCTCCC | GAGTCTT | 1680 |
| CCCACATTCA | AGAGGGCCGC | TGGGTGCATC | CTTACCCAGC | TATCCTTACA | GTGTTTG | 1740 |
| ATGGGGAATG | GCTCTGTCTT | ACTGTGGGCA | TGGTGGGCAT | TTTTGGCAGT | GGGAGAG | 1800 |
| GAAAATCTGT | TGATTAGAAG | CTCAGTATGT | TAATTCGACT | CCAGGACAGC | TTTCAGA | 1860 |
| AGTGGCTAAG | AGAAGAACGA | GGTCCCAGGG | GATCTCTTGA | GGTGACTTAT | TTTGACA | 1920 |
| TTTGGGAAAG | TTATCTAGGA | GATTTGTTCC | ATAACTCATT | TTCCCATACT | CTGGTGA | 1980 |
| ATTTACTGAG | TGTATCGGTC | CCACTGAGCC | AGTGCATAGC | ATGGTAACAA | ACAGTTC | 2040 |
| ATTATCAATG | ACTTAACAGA | ATTAACTAAA | TTAACAAAAG | TTACTTTCTC | ACTTGTA | 2100 |
| AATATCTATA | ATGTATGGGC | TCAGGCTTCT | GCATTTTATA | CTCAGGATTC | TAGACTG | 2160 |
| GAGAAGTTGC | CATGTGGGGG | AACATTGATG | GATACTGTGA | TAAAGCAGAA | GAAAGCT | 2220 |
| AGGAGTCTTG | CATAGGCAAT | GCACTGTGGC | TCAAAAATGA | CACCCATCAC | TTTGTCT | 2280 |
| TCTTTATTGA | TCAAAACTAA | TTAATGCCTC | CAACCAAACA | AAAGTGGCCA | AGAAATG | 2340 |
| GTCTACCTTG | TGTCTCAAAA | CAGAGGATGG | AGAATATTTG | GTGAAAATTA | CCATGAC | 2400 |
| CACATGGCCA | CGTAGGTCTT | TATAATGACA | GAGCTAGCAT | TTGTCACATT | GACCAAG | 2460 |
| TGTCCATACA | CTCTACAGTA | ATGATGAGTC | CTCAGTGCAC | AGGGGAGGAT | GCTGAAG | 2520 |
| CAGGACAGCA | TCCTCCAGAC | ACATAAGACT | TCAGAGCAGA | GGGATTCTCC | CTCCACC | 2580 |
| CGCAATTCCT | TGCTTTCTCC | TAACTTCCTT | TACAAAGTCA | TGCTTGGAAA | TGTCTAT | 2640 |
| TCATCATGTG | GCTCATTTTT | TTCTCTGTTC | ATTTTTTTTC | CCCAAAATTC | AGCTTCT | 2700 |
| CCAACCACCT | GCTGCTTTAA | CCTGGCCAAT | AGGAAGATAC | CCCTTCAGCG | ACTAGAG | 2760 |
| TACAGGAGAA | TCACCAGTGG | CAAATGTCCC | CAGAAAGCTG | TGATGTAAGT | AAATAAA | 2820 |
| CACCCTCCCC | TAGACAAAAA | AATAATGTCT | AGGGCACAGA | GTCAAGAACT | GTGGGAG | 2880 |
| TAGACTCTGA | TAGTTTGACC | TCTATGGTCC | AATTCATTAA | TTTTCACAAG | TGAGTGT | 2940 |
| CTCCCAGCTC | CCTGCCTGGG | AGATTGCTGT | AGTCATATCA | ATTTCTTCAA | GTCAAGA | 3000 |
| AAGATGGTTT | TACTGGGCCT | TTAAGAGCAG | CAACTAACCC | AAGAGTCTCA | TCCTTCC | 3060 |
| TCTCCGTAGC | AACCCTTTGT | CCAGGGGCAG | ATGGTCCTTA | AATATTTAGG | GTCAAAT | 3120 |
| CAGAATTTTC | AAAAACAATC | CTTCCAATTG | CATCCTGATT | CTCCCCACAG | CTTCAAG | 3180 |
| AAACTGGCCA | AGGATATCTG | TGCCGACCCC | AAGAAGAAGT | GGGTGCAGGA | TTCCATG | 3240 |
| TATCTGGACC | AAAAATCTCC | AACTCCAAAG | CCATAAATAA | TCACCATTTT | TGAAACC | 3300 |
| CCAGAGCCTG | AGTGTTGCCT | AATTTGTTTT | CCCTTCTTAC | AATGCATTCT | GAGGTAA | 3360 |
| CATTATCAGT | CCAAAGGGCA | TGGGTTTTAT | TATATATATA | TATATATATT | TTTTTTT | 3420 |
| AAAAAACGTA | TTGCATTTAA | TTTATTGAGG | CTTTAAAACT | TATCCTCCAT | GAATATC | 3480 |
| TATTTTTAAA | CTGTAAAGCT | TTGTGCAGAT | TCTTTACCCC | CTGGGAGCCC | CAATTCG | 3540 |
| CCCTGTCACG | TGTGGGCAAT | GTTCCCCCTC | TCCTCTCTTC | CTCCCTGGAA | TCTTGTA | 3600 |
| GTCCTGGCAA | AGATGATCAG | TATGAAAATG | TCATTGTTCT | TGTGAACCCA | AAGTGTG | 3660 |
| CATTAAATGG | AAGTAATGTT | GTTTTAGGAA | TACATAAAGT | ATGTGCATAT | TTTATTA | 3720 |

-continued

```
TCACTAGTTG TAATTTTTTT GTGGGAAATC CACACTGAGC TGAGGGGGAC AAAGATG          3780

GTGGCCAAGA GGGGCTTGGT TAAGGGGGTG GGAACTATGT CCCTGGGAAA TGAGTTT          3840

GCTTAGCTGG TCTTCATTGA AATGCAGGGT GAAACTGACA AACCCATTCC AGCCCTC          3900

TCCCATTTTC AACAGTATTT CCCAGACCCC AAACTTCAGC CACGAAAATA TCTGGAG          3960

TGCCACCATT CCTTTCCTCC CCACCTCATA CTTGCCTCTC CTGGGACCTA TTTTAAC          4020

CCTGTGGTAT CTCCCTCTAC CCGACCCTGC TCCTCGGTCT TCCAACCCAG ACTAGGC          4080

CATGACAGAC ACTGGAAATC AGAGGAAGGC TAGGTGACC                              4119
```

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 2:

```
AGAAACCACC ACCTCTCACG                                                     20
```

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 3:

```
GAGAATTTGC AGTGAGTCTG T                                                   21
```

(2) INFORMATION FOR SEQ ID NO: 4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 4:

```
GGGGCTTACC TGGCCCAAC                                                      19
```

(2) INFORMATION FOR SEQ ID NO: 5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 5:

```
GGGGCTTACC TGGCCCAAT                                                      19
```

-continued (2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 6:

TCAAGGAAGG TTCTTAGATC G                  21

METHODS FOR DIAGNOSIS, PREDICTION AND TREATMENT OF ASTHMA AND OTHER INFLAMMATORY CONDITIONS BASED ON EOTAXIN CODING SEQUENCE POLYMORPHISM

RELATED APPLICATIONS

This application is a divisional of U.S. patent application Ser. No. 09/076,259, filed on May 12, 1998, now U.S. Pat. No. 6,548,245, which claims priority under Title 35, United States Code, §119(e), of U.S. Provisional Application 60/046,720, filed May 16, 1997, and entitled "Methods for Diagnosis, Prediction and Treatment of Asthma and Other Inflammatory Conditions Based on Eotaxin Coding Sequence Polymorphism", the entire contents of which are incorporated herein by reference.

SPONSORSHIP

This invention resulted from research sponsored, in part, by NIH Grant Number HL0328. The Government has certain rights in this invention.

BACKGROUND OF THE INVENTION

This invention pertains to disease diagnosis, prediction and treatment and, more particularly, to diagnosis, prediction and treatment of asthma, rhinitis and other inflammatory conditions associated with eosinophil accumulation in respiratory and other tissues.

Asthma is a respiratory ailment characterized by airway obstruction, inflammation and/or hyper-responsiveness. According to a 1994 survey by the U.S. Department of Health and Human Services, over 12 million Americans suffer from asthma, almost 5 million of them under the age 18. Long-term medications include corticosteroid, beta-agonists and leukotriene modifiers. For quick relief, anticholinergics, corticosteroids, and/or beta-agonists may be applied. Adverse side effects of these treatments include cough, dysphonia, candidiasis (corticosteroids), tachycardia, muscle tremor, hypokalemia, hyperglycemia (beta-agonists), liver impairment (leukotriene modifiers), drying of mouth and respiratory secretions (anticholinergics).

The standard of care for asthma dictates that treatment with the foregoing medications be a guided by disease severity of the symptoms. Since the nature of asthma is to have exacerbations and remissions, this approach under-treats patients with the potential to develop significant airway inflammation, but who at the time of pulmonary function testing are in a physiological remission. In addition, this approach can result in application of medications of greater toxicity then truly required for the condition.

One characteristic of inflammatory reactions, such as asthma and rhinitis, is the accumulation of eosinophils in the mucosal lining of the affected organs. Recruitment of eosinophils is thought to be mediated by a class of proteins known as chemokines and, particularly, by the protein eotaxin. That ligand is understood to have a high affinity for so-called CC-CKR3 receptors, which are found in large numbers on the surfaces of eosinophils.

In view of the foregoing, an object of this invention use to provide improved compounds and methods for prediction, diagnosis and treatment of disease and, more particularly, improved compounds and methods for prediction, diagnosis and treatment of asthma, rhinitis and other inflammatory conditions of respiratory and other tissues.

A further object of the invention is to provide such improved compounds and methods as permit control of such inflammatory conditions without undue risk of under- or overtreatment.

Yet another object of the invention is to provide such improved compounds and methods as permit prediction, diagnosis and treatment of such inflammatory conditions in a cost effective manner.

SUMMARY OF THE INVENTION

The foregoing objects are among those attained by the invention, which facilitates prediction, diagnosis and treatment of inflammatory conditions through exploitation of a heretofore unknown association between those conditions and a polymorphism of the eotaxin gene.

Thus, for example, the invention provides a method for diagnosis of asthma based on identification a substitution of adenine for guanine 67 base pairs following the ATG initiation codon (initiating counting at the A in that codon) of the eotaxin gene or, alternatively, based on identification of a substitution of threonine for alanine in the 23rd position of the resulting protein. The wild type (normal) eotaxin gene (i.e., without the aforementioned polymorphic substitution) is shown as SEQ ID NO: 1, below.

In a related aspect, the invention provides methods for prediction or diagnosis of asthma or other inflammatory conditions associated with tissue accumulation of eosinophils, such rhinitis and atopy, based on diagnosis of the foregoing substitutions.

Further aspects of the invention provide methods as described above in which the adenine/guanine substitution is identified by analysis of DNA or mRNA (or on other nucleic acid sequences, such as cDNA, developed therefrom) in tissue, blood or other biological samples taken from a patient or kindred thereof. Such analysis can include sequencing or probing those sequences using otherwise known techniques, as adapted to identify the aforementioned polymorphism.

In one preferred aspect of the invention, the nucleotide sequences in the samples are amplified, e.g., via polymerase chain reaction (PCR), and the amplified product is analyzed for evidence of the substitution. Such amplification can be performed, e.g., using conventional PCR or, preferably, using single-strand conformation polymorphism (SSCP) and/or amplification refractory mutation system (ARMS) techniques, though other amplification techniques known in the art can be used as well.

Further aspects of the invention provide methods as described above in which the threonine/alanine substitution is identified by contacting the biological samples with immunolabelling agents, such as monoclonal or polyclonal antibodies, raised against the variant protein (i.e., the protein resulting from the eotaxin gene with the aforementioned adenine/guanine substitution).

Still other aspects of the invention provide novel chemical compounds, notably, nucleic acid sequences for use in the diagnosis, prediction and/or treatment of the aforementioned inflammatory conditions.

BRIEF DESCRIPTION OF THE DRAWINGS

A more complete understanding of the invention may be attained by reference to the drawings, in which.

DESCRIPTION OF THE SEQUENCES

Figure 1:
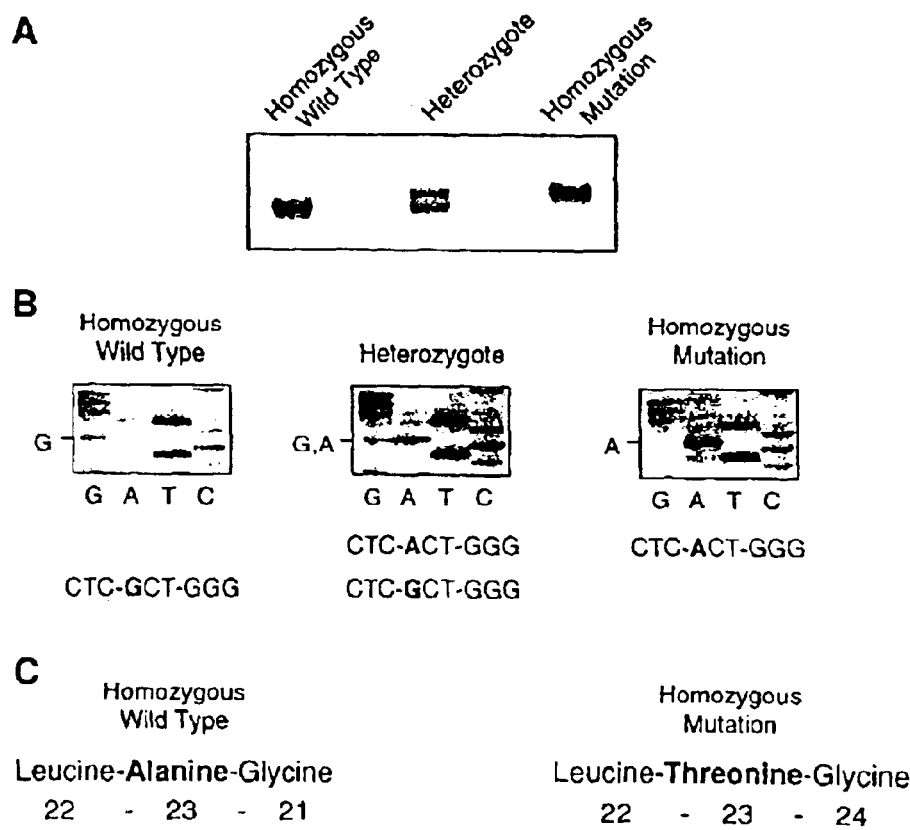
FIG. 1A depicts a portion of an electrophoretic pattern resulting from SSCP analysis of lymphocyte density gradient enriched fractions of fresh whole blood from normal and asthmatic patients.
FIG. 1B depicts a portion of an electrophoretic pattern resulting from di-deoxy DNA sequencing of DNA from normal and asthmatic patients.
FIG. 1C depicts the threonine/alanine substitution in the cotaxin protein sequence resulting from the adenosine/guanidine in the eotaxin gene.

SEQ ID NO: 1 is the wild type (normal) sequence for the human eotaxin gene;

SEQ ID NO: 2 and SEQ ID NO: 3 are oligonucleotide sequences used in one practice of the invention as primers for PCR and/or SSCP analysis of nucleotide sequences; and SEQ ID NO: 4, SEQ ID NO: 5 and SEQ ID NO: 6 are oligonucleotide sequences used in one practice of the invention as primers for ARMS analysis of nucleotide sequences.

DETAILED DESCRIPTION OF THE ILLUSTRATED EMBODIMENT

A genetic contribution to the pathogenesis of asthma has long been inferred from the increased prevalence of asthma in families. The association of genetic markers with airway hyper-responsiveness, a defining physiological feature of asthma, in affected kindreds implies that genetic factors can influence asthma pathogenesis (1)*. That specific genetic polymorphisms are associated with the asthma phenotype is supported by a growing number of association studies. Many of these studies have been undertaken because there is reason to believe that the target genes are relevant to pathogenesis or severity of allergic diseases including asthma (2). For example it is now known that differences in the post stimulation presence of the beta-adrenergic receptor on isolated cells in vivo are related to polymorphic variants of the beta-adrenergic receptor gene (3–5) and that the occurrence of one polymorphic form of the $\beta_2$ adrenergic receptor ($\beta_2$AR) is associated with airway hyperresponsiveness in vivo. Further, this polymorphism has been associated with the nocturnal and steroid requiring form of asthma (6,7). The relevance of genetic polymorphisms to asthma is further supported by the association of polymorphisms in the 5-lipoxygenase gene (8), and the IL-4 gene (9,10) with the asthma phenotype. Awareness and analysis of asthma relevant genetic polymorphisms has the potential to allow the development of treatment strategies that are guided by genetic analysis.

*Numeric expressions in parenthesis refer to publications and other disclosures listed in the endnotes, the teachings of which are incorporated herein by reference.

It is now widely recognized that asthma is a disease of airway inflammation and that eosinophils and their products are present in the airways of mild as well as severe asthmatics (11–14). The airway presence of eosinophils may be important in asthma because eosinophil products can disrupt airway function (15–17). Interestingly, therapeutic responses to asthma treatment are associated with a decrement in the presence of eosinophils and their products (18–20). The recent discovery of the CCK-3 receptor on eosinophils and its specific ligand eotaxin has defined a novel mechanism by which eosinophils can be recruited into the airways (21–23). Immunohistochemical studies of inflamed and adjacent non-inflamed upper airways have associated eotaxin with the presence of eosinophils (24).

Based on these associations and the identification of eotaxin CDNA sequence variants in a mixed population of dermal fibroblasts (25), we have discovered a polymorphism in the coding region of the eotaxin gene that correlates with the incidence of asthma. The wild type (normal) eotaxin gene is shown below as SEQ ID NO: 1. The polymorphism that we have discovered comprises substitution of adenine for guanine 67 base pairs following the ATG initiation codon (initiating counting at the A in that codon) of the gene. The variant eotaxin protein produced by that polymorphism incorporates the amino acid threonine in its 23rd position, in lieu of the amino acid alanine that occupies that position in the normal eotaxin protein.

One embodiment of our invention comprises detecting asthma by identifying this polymorphism in DNA or mRNA (or on other nucleic acid sequences, such as cDNA, developed therefrom) contained in tissue, blood or other biological samples taken from a patient. The polymorphism can be detected in any manner conventionally known in the art, e.g., via directly sequencing the nucleotide sequences contained in the samples, though it is preferably detected by, first, amplifying those sequences, e.g., via polymerase chain reaction (PCR).

Alternatively, or in addition, the disease can be detected by identification of the variant protein in those tissues. Such diagnosis—or even prediction—can also be made by identifying the polymorphism or variant protein in samples taken from kindred or other relatives of a human being. This can be helpful, for example, in determining whether offspring are likely to be genetic predisposed to the condition, even though it has not expressed itself in the parents.

In one preferred embodiment of the invention, amplification and detection is using single-strand conformation polymorphism (SSCP) and/or amplification refractory mutation system (ARMS) techniques, though other amplification techniques known in the art can be used as well.

Where conventional PCR or SSCP are used, preferred primers include the oligonucleotides

| AGAAACCACCACCTCTCACG | (SEQ ID NO: 2) |
| and | |
| GAGAATTTGCAGTGAGTCTGT | (SEQ ID NO: 3) | or functional equivalents thereof. Where the ARMS technique is used, the forward primers can include

| GGGGCTTACCTGGCCCAAC | (SEQ ID NO: 4) |
| and | |
| GGGGCTTACCTGGCCCAAT | (SEQ ID NO: 5) | or functional equivalents thereof. The reverse primer for the ARMS technique can include

| TCAAGGAAGGTTCTTAGATCG | (SEQ ID NO: 6) | or functional equivalents thereof.

In further embodiments, the invention provides for treatment of asthma by detecting and remediating (e.g., via conventional gene therapy techniques) the genomic polymorphism either systemically or in the affected tissues. Alternatively, such treatment may be attained through detection of the polymorphism or variant protein, and by application of appropriate medications, e.g., for blocking the CCK-3 receptor.

In addition to asthma, the invention can be applied to the diagnosis, prediction and/or treatment of rhinitis, atopy, and other inflammatory diseases associated with accumulation of eosinophils in the mucus or tissues. The foregoing techniques can likewise be applied to other mammals that synthesize, utilize and/or metabolize eotaxin in a manner similar to that of humans.

EXAMPLE

Detection of Eotaxin Polymorphisms in Patients Suffering from Asthma

Patient Materials: The American Thoracic Society criteria for the diagnosis of asthma were met in 128 subjects who had disease of varying severity. Normal subjects were defined by the absence of detected medical disease and a negative history for asthma and atopy. In addition, each of the 81 normal subjects failed to react to the intra-dermal injection of 12 common aero-allergens. The source of DNA for single-strand conformation polymorphism (SSCP) analysis was a lymphocyte density gradient enriched fraction of fresh whole blood that was immortalized using a standard Epstein Barr virus protocol (26,27). These cells were obtained from 25 normal subjects and 25 subjects with asthma treated only with inhaled beta-agonists. For the amplification refractory mutation system (ARMS) technique, additional DNA was harvested from the whole blood of 35 mild asthmatics, 28 subjects with near fatal asthma, one subject with fatal asthma and 56 normal subjects. DNA was isolated by buccal brushing from an additional 39 subjects with steroid requiring asthma. DNA was extracted using a commercially available kit according to the instructions of the manufacturer (Stratagene, La Jolla, Calif.).

PCR: Twenty and 21 base oligimers were synthesized using an Abacus DNA synthesizer, the sequence of these oligimers was AGAAACCACCACCTCTCACG (SEQ ID NO: 2) and GAGAATTTGCAGTGAGTCTGT (SEQ ID NO: 3) respectively. PCR was performed using 20 µl reaction volumes containing 10 mM Tris.HCl, 50 mM KCl, 0.1 µl genomic DNA, a primer concentration of 2 µM, and 2.5 mM $MgCl_2$ and covered with oil. The reaction mixture was denatured at 95° C. for 5 min and placed at 80° C. All four dNTPs were added to a final concentration of 0.2 mM including 1.25 µCi of (P)dATP. After the addition of 2.5 units of AmpliTaq DNA polymerase (Perkin-Elmer/Cetus) 25 cycles of PCR were preformed with a 2 minute 55° C. annealing segment followed by a 3 minute 72° C. extension segment and a 1 minute 94° C. denaturation segment a 7 minute 72° C. extension segment followed the final cycle.

SSCP: SSCP was performed by the method of Beier (28). Briefly, the PCR solution was diluted 1.5:10 in a stop solution of 100% formamide containing xylene cyanol and bromophenol blue, denatured for 5 minutes at 94° C. and placed on ice. a 4 µl sample was loaded on to an MDE gel (AT Biochem, Malvern Pa.) and subjected to a 5 to 6 hour electrophoresis at 4° C. in 0.6×TBE at 60 W constant power. The PCR products were transferred from the gel to filter paper, dried, and subjected to autoradiography overnight with an intensifying screen.

ARMS: The presence or absence of a 530 bp band was determined for paired PCR reactions under the following conditions. The sequences of the forward primers were GGGGCTTACCTGGCCCAAC (SEQ ID NO: 4) and GGGGCTTACCTGGCCCAAT (SEQ ID NO: 5) respectively and the sequence of the reverse primer was TCAAGGAAGGTTCTTAGATCG (SEQ ID NO: 6). Each 20 µl reaction contained 0.1 µg of DNA, 2.0 mM $MgCl_2$, a 0.2 mM dNTP mixture, and 0.5 µM primers. Each reaction was subjected to the following amplification procedure: denaturation at 94° C. for 5 minutes, addition of 2.0 units of AmpliTaq DNA polymerase, annealing at 56° C. for 30 seconds, extension at 72° C. for 1 minute, and denaturation at 94° C. for 40 seconds. Thirty amplification cycles were followed by a 5 minute 72° C. segment extension period. The electrophoretic mobility of the reaction products was determined on a 2% agarose gel. The ARMS band detection pattern corresponded to the sequence and SSCP determined genotype for each of the 50 samples studied.

DNA Sequencing: The eotaxin DNA sequence of each of the 25 asthmatic and 25 normal subjects was determined by cycle sequencing PCR generated fragments from these subjects. PCR was performed for 20 cycles as described above but using non-radiolabeled dATP. Cycle sequencing was performed using a commercially available kit according to the instructions of the manufacturer (Life Technologies, Gaithersburg, Md.).

Results

SSCP analysis demonstrated three distinct electrophoretic patterns presented in FIG 1A. a single distinct band was noted in lanes corresponding to 18 of the normal subjects and 2 bands were noted in 7 of these subjects. A single band with the same electrophoretic mobility of the single band noted in normal subjects was present in 15 of the lanes corresponding to asthmatic subjects. Seven lanes from asthmatic subjects demonstrated 2 bands and 3 lanes had a single band with different electrophoretic mobility. Di-deoxy DNA sequencing of the relevant DNA from each of these 50 subjects revealed 3 distinct sequence patterns that corresponded exactly with the SSCP patterns, a single base pair substitution polymorphism was detected 67 base pairs in the 3' direction from the ATG initiation codon of the eotaxin gene, FIG. 1B. This polymorphism would alter the predicted eotaxin protein sequence by replacing the alanine at position 23 with the polar amino acid threonine (C). The normal subjects all had at least one allele containing a guanidine residue. This sequence is the known eotaxin sequence. Three of the asthmatic subjects were homozygous for a variant form of eotaxin that had an adenosine residue at this locus.

Figure 2:
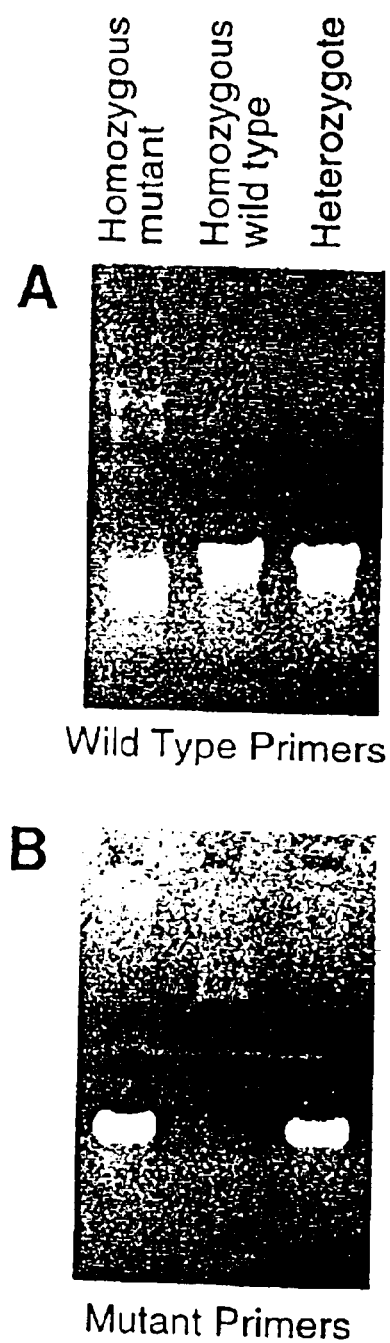
FIG. 2 depicts a representative set of gels demonstrating the presence or absence of a 530 bp PCR product from pairs of reactions.

Using the ARMS technique we determined the frequency of the homozygous form of this polymorphism in 128 asthmatic subjects and 81 normals. We found that a significantly higher frequency of this polymorphism in asthmatic compared to normal subjects, Table I ($\chi^2$, p<0.05). a representative set of gels demonstrating the presence or absence of a 530 bp PCR product from pairs of reactions is presented in FIG. 2.

|  | Homozygous Mutant | Non-Homozygous Mutant |
| --- | --- | --- |
| Normals | 0 | 81 |
| Asthmatics | 6 | 128 |

Discussion

We have detected a polymorphism in the eotaxin gene at a position that alters the predicted sequence of the translated protein product at a locus near the site where the "leader" sequence is removed. This finding is in accord with the detection of an eotaxin variant in a mixed population of dermal fibroblasts (25). In contrast to that report, our finding that different forms of the eotaxin gene are present in different individuals establishes the existence of this eotaxin polymorphism and its higher frequency of its homozygous form in patients with asthma.

This codon 69 single base pair substitution of an adenosine for a guanidine residue 67 base pairs after the ATG initiation codon alters the predicted protein sequence of eotaxin by substituting the polar amino acid threonine for the hydrophobic amino acid alanine. This alteration occurs at human eotaxin amino acid position 23. The presence of this sequence alteration near the terminus of the hydrophobic leader sequence suggests that it may alter the rate or pattern of eotaxin processing relative to its secretion.

The potential biological role of eotaxin for recruiting eosinophils to the airways after allergic stimulation (21,23, 24,29) similar to that which occurs in asthma suggested that altered forms of eotaxin may be relevant to asthma. We therefore compared the frequency of the polymorphism in well characterized asthmatics to that of non-atopic normals. We found that 30% of our population of non-atopic normals and 25% of our asthmatics are heterozygous for this polymorphism. Interestingly 5% of our asthmatic population was homozygous for this polymorphism while we did not detect any homozygotes in our population of normals. We did not observe, but were unlikely to detect, any association of this polymorphism with asthma severity.

The effect of the presence of this polymorphism on eosinophil biology remains incompletely investigated. We have observed increased numbers of eosinophils in the peripheral blood of asthmatic subjects that are homozygous for this polymorphism suggesting that it may enhance eosinophil recruitment into the blood or prolong eosinophil survival. Alternatively, the lack of the wild type form of eotaxin may inhibit the egress of eosinophils from the blood into the tissues.

In summary, we have discovered that a polymorphism in the eotaxin gene and resultant variant in the eotaxin protein that can be exploited for purposes of diagnosis, prediction and treatment of asthma, rhinitis and other inflammatory conditions.

The list of references is presented below and is followed by the Sequence Listing and What is Claimed.

What is claimed is:

1. A composition comprising an isolated nucleic acid consisting of the wild type normal eotaxin gene sequence as shown in SEQ ID NO: 1, wherein said nucleic acid includes a guanine to adenine substitution 67 base pairs following the ATG initiation codon of the wild type normal eotaxin gene, whereby counting is initiated at the A in that codon.

2. A composition comprising an isolated oligonucleotide consisting of a nucleotide sequence selected from the group consisted of:

| | |
|---|---|
| AGAAACCACCACCTCTCACG; | (SEQ ID NO: 2) |
| GAGAATTTGCAGTGAGTCTGT; | (SEQ ID NO: 3) |
| GGGGCTTACCTGGCCCAAC; | (SEQ ID NO: 4) |
| GGGGCTTACCTGGCCCAAT; and | (SEQ ID NO: 5) |
| TCAAGGAAGGTTCTTAGATCG. | (SEQ ID NO. 6). |

* * * * *